(12) United States Patent
D'Addario

(10) Patent No.: US 12,740,788 B2
(45) Date of Patent: Sep. 22, 2026

(54) VENOUS VALVE APPARATUSES AND METHODS FOR CONTROLLING BLOOD FLOW

(71) Applicant: Justin D'Addario, St. Louis, MO (US)

(72) Inventor: Justin D'Addario, St. Louis, MO (US)

( * ) Notice: Subject to any disclaimer, the term of this patent is extended or adjusted under 35 U.S.C. 154(b) by 1176 days.

(21) Appl. No.: 17/737,214

(22) Filed: May 5, 2022

(65) Prior Publication Data

US 2022/0361884 A1 Nov. 17, 2022

Related U.S. Application Data

(60) Provisional application No. 63/189,302, filed on May 17, 2021.

(51) Int. Cl.
*A61B 17/122* (2006.01)
*A61B 17/00* (2006.01)

(52) U.S. Cl.
CPC .. *A61B 17/122* (2013.01); *A61B 2017/00022* (2013.01); *A61B 2017/00398* (2013.01); *A61B 2017/00734* (2013.01); *A61B 2017/00778* (2013.01)

(58) Field of Classification Search
None
See application file for complete search history.

(56) References Cited

U.S. PATENT DOCUMENTS 5,267,565 A * 12/1993 Beard ...................... A61B 8/06 600/500
7,766,814 B2 * 8/2010 Walsh ................. A61M 60/468 600/16
8,696,543 B2 * 4/2014 Forsell ................ A61M 60/289 600/37
9,554,724 B2 * 1/2017 Schuessler ........... A61B 5/0295
10,076,462 B2 * 9/2018 Johnson ............... A61B 5/4842
10,166,164 B2 * 1/2019 Johnson ................. A61H 7/001
2014/0243857 A1 * 8/2014 Miller ................ A61B 17/1285 606/157
2021/0330544 A1 10/2021 Ahn et al.

FOREIGN PATENT DOCUMENTS

AU 2014262372 A1 * 11/2015 ........... A61B 17/135
CN 110101422 A * 8/2019 ......... A61B 17/0643
CN 120420041 A * 8/2025
JP 2025510731 A * 4/2025 ........... A61B 8/4477
WO WO-2005084730 A1 * 9/2005 .......... A61M 60/289
WO WO-2009048377 A1 * 4/2009 .......... A61M 60/191
WO WO2014/182849 11/2014

* cited by examiner

*Primary Examiner* — Joanne M Rodden
(74) *Attorney, Agent, or Firm* — Harness, Dickey & Pierce, P.L.C.

(57) ABSTRACT

Valve apparatuses and methods are provided for controlling blood flow in a vein of an individual. One example valve apparatus includes at least one valve member configured to be positioned adjacent to an exterior surface of a vein of an individual and outside of a lumen of the vein, at least one sensor configured to be positioned adjacent to the exterior surface of the vein, and a controller configured to receive, from the at least one sensor, a signal representing one or more characteristics of blood flow through the lumen, determine a direction of the blood flow based on the one or more characteristics, and in response to the determined direction of the blood flow being away from a heart of the individual, activate the at least one valve member to occlude blood flow through the lumen away from the heart.

17 Claims, 7 Drawing Sheets

VENOUS VALVE APPARATUSES AND METHODS FOR CONTROLLING BLOOD FLOW

CROSS-REFERENCE TO RELATED APPLICATION

This application claims the benefit of, and priority to, U.S. Provisional Application No. 63/189,302 filed on May 17, 2021. The entire disclosure of the above-referenced application is incorporated herein by reference.

FIELD

The present disclosure generally relates to venous valve apparatuses configured to control blood flow (e.g., in veins, etc.), and to related methods for controlling such blood flow.

BACKGROUND

This section provides background information related to the present disclosure which is not necessarily prior art.

Individuals have circulatory systems including arteries for carrying blood away from the heart and veins for carrying blood towards the heart. The veins include one-way valves to prevent retrograde blood flow. Some individuals suffer from venous-associated conditions such as, for example, deep venous insufficiency (DVI) due to defects in the walls, valves, etc., of the veins. These conditions may result in swelling, chronic pain, etc. It is known to treat DVI with compression garments as a non-surgical option, or with valvuloplasty, external banding, autologous valve transplantation and/or valve transposition as surgical options.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. The description and specific examples included herein are intended for purposes of illustration only and are not intended to limit the scope of the present disclosure.

Individuals may experience venous reflux, venous hypertension, and/or other issues associated with the venous system. These issues may occur when one-way valves within veins malfunction thereby allowing retrograde blood flow to pass through the valves and away from the heart. Consequently, individuals may be afflicted with conditions, such as deep venous insufficiency (DVI), resulting in swelling, chronic pain, etc. While DVI is not generally life threating or overly damaging to overall health, individuals may experience significant discomfort. Although compression garments can be worn to address DVI in some individuals, these garments are often bothersome and decrease the quality of life of the individuals. Additionally, surgical options for treating DVI are difficult procedures and have limited clinical effectiveness. Further, these surgical options are particularly invasive as they require placing valves within the veins (e.g., in lumens of the veins, etc.). What's more, such actions routinely cause thrombosis (e.g., the clotting of blood, etc.) and/or require lifelong anti-coagulation treatments. As such, the surgical options for treating DVI have a significant cost of intervention, but are often necessary to prevent complications of chronic DVI.

Uniquely, the valve apparatuses and methods herein provide for surgical options for treating certain conditions, such as, for example, DVI, lymphedema, chronic wounds, etc., experienced by individuals, by placing valves on the outside of the veins. In particular, through a limited invasive surgery on an individual, one or more controllable valves may be positioned along an exterior surface of one or more veins (e.g., along exterior wall surfaces of the veins, etc.), and activated, actuated, operated, etc. to occlude retrograde blood flow through the veins and/or to assist in pumping blood back to the heart. Because the valves are positionable outside the veins, and not within the lumens of the veins, there is a reduced, if not eliminated, risk associated with thrombosis and/or an elimination of anti-coagulation treatments as required in other surgical treatments.

Figure 1:
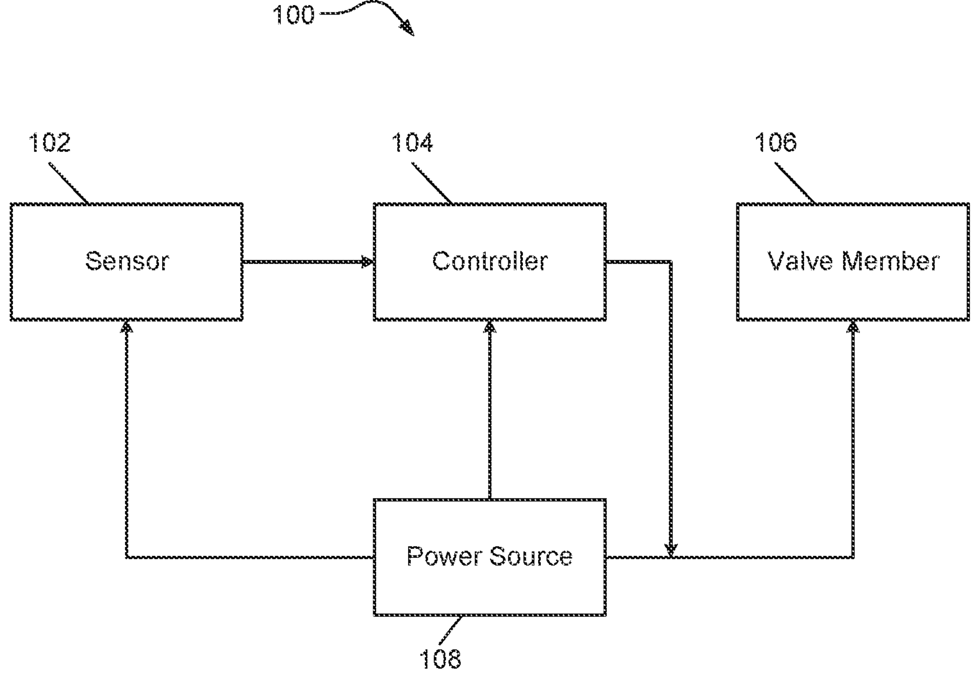
FIG. 1 is a block diagram of an example valve apparatus of the present disclosure, where the valve apparatus includes a valve member suitable for controlling blood flow in a vein of an individual.

FIG. 1 illustrates an example valve apparatus 100 in which one or more aspects of the present disclosure may be implemented. The valve apparatus 100 may be used in a human, an animal, etc. Although the valve apparatus 100 is presented in one arrangement, other embodiments may include valve apparatuses arranged otherwise depending on, for example, the number and/or types and/or configurations of controllable valve members and/or sensing devices employed in connection therewith.

In the illustrated embodiment, the valve apparatus 100 generally includes a sensor 102, a controller 104 in communication with the sensor 102, a valve member 106, and a power source 108. As shown in FIG. 1, the controller 104 is configured to receive an input signal from the sensor 102 representing one or more characteristics of blood in a vein (e.g., pressure, flow, etc.), and provide an output signal (e.g., a control signal, etc.) for controlling the state of the valve member 106. The power source 108 (e.g., a battery, etc.) is configured to provide power to the sensor 102, the controller 104, and the valve member 106 via wires or otherwise. Although the apparatus 100 is shown with one sensor 102 and one valve member 106 in FIG. 1, it should be appreciated that more than one sensor and/or more than one valve member may be employed. For example, the apparatus 100 may include two sensors positioned at different locations relative to the valve member 106, two valve members positioned along a vein at different locations, three valve members positioned along the vein at different locations, etc.

Any one or all of the components of the valve apparatus 100 shown in FIG. 1 may be positionable within a body of an individual. For example, the sensor 102, the controller 104, and the valve member 106 may be surgically positioned along an exterior wall surface of a vein extending between the heart and a limb (e.g., a leg, etc.) in the body. Additionally, the power source 108 may be surgically positioned in a subcutaneous tissue of the individual (e.g., adjacent to an inner surface of the skin, etc.). In such examples, the sensor 102, the controller 104, and the valve member 106 are positionable adjacent to the outer surface of the vein, and the power source 108 is positionable remote from the vein. With this arrangement, wires or other connections extending between the power source 108 and the other components are configured to route entirely within the body. In other examples, the power source 108 may be positionable adjacent to the outer surface of the vein (e.g., near the sensor 102, the controller 104, and/or the valve member 106, etc.), outside the body, etc. If the power source 108 is positioned outside the body, wires extending between the power source 108 and the other components must pass through the skin. It should be appreciated that the position of the power supply may be based on, for example, a manner to charge or recharge the power supply, if or as needed, and/or a type of the power supply, and/or a type of interconnection or interaction between the power source 108 and the other components of the valve apparatus 100.

The sensor 102 of the valve apparatus 100 is configured to sense one or more characteristics of blood flow through a lumen of the vein. The sensor 102 may then be configured to provide, to the controller 104, one or more signals (e.g., via a wired connection, a wireless connection, etc.) representing the characteristics to allow the controller 104 to determine the direction of blood flow. In some examples, the sensor 102 may include one or more inferential sensors configured to sense one or more characteristics (e.g., pressure levels, flow rates, etc.) of the direction of the blood flow through the lumen of the vein. For example, the sensor 102 may include one or more pressure sensors (e.g., one or more piezoelectric pressure sensors, etc.) to detect pressure levels associated with the lumen and/or vein, for example, on opposing sides of the valve member 106. In other examples, the sensor 102 may include one or more other suitable sensors (e.g., an ultrasonic flow meter including multiple transducers configured to receive and/or transmit ultrasonic waves passing through the blood, a Doppler shift sensor, etc.) for sensing another characteristic (e.g., a flow rate, etc.) of blood flow in the lumen. In connection therewith, and as generally indicated above, the sensor 102 is thus configured to be positioned relative to the lumen of the vein to achieve and/or sense such characteristic(s) of the blood flow.

In this example embodiment, the controller 104 includes a microcontroller and/or any other suitable processing device capable of the functions described herein. In some examples, the controller 104 is configured to determine the direction of blood flow in the vein based on input from the sensor 102 and then to control the state of the valve member 106. For example, the controller 104 may be configured to determine, based on signals from the sensor 102, the direction of blood flow based on different characteristics of blood flowing through the lumen, a pressure associated with such blood flow, etc. For example, if the pressure level on the heart side of the valve member 106 is greater than the pressure level on the limb side of the valve member 106, then the controller 104 may be configured to determine that blood flow through the lumen is traveling away from the heart. In other examples, the controller 104 may be configured to detect the direction of blood flow based on a flow rate of the blood passing through the lumen, etc.

In response to detecting the direction of blood flow in the vein (and/or lumen), the controller 104 may be configured to provide a signal (e.g., a control signal, etc.) (e.g., via a wired connection, a wireless connection, etc.) to activate or deactivate the valve member 106. For example, the controller 104 may be configured to provide a signal to activate the valve member 106 when blood is detected as flowing away from the heart, whereby the valve member 106 is configured to occlude the blood flow through the lumen of the vein. The controller 104 may then be configured to provide a signal to deactivate the valve member 106. In connection therewith, the signal provided by the controller 104 may control the state of the valve member 106 by controlling when power is provided to the valve member 106.

With continued reference to FIG. 1, as described, the valve member 106 (e.g., when activated, actuated, operated, etc.) is configured to occlude blood flow through the lumen of the vein. In particular, in this embodiment, the valve member 106 includes one or more electromagnets, pistons, actuators, constrictors, and/or any other suitable device or member, which are structured to compress (or constrict, etc.) the vein, when activated, to occlude blood flow through the lumen of the vein. For example, the valve member 106 may include an electromagnet (or multiple electromagnets) positioned on one side of the vein, and the apparatus 100 may further include a magnetic structure (or multiple magnetic structures) on the opposing side of the vein. In such example, the electromagnet(s) and the magnetic structure(s) may be configured to compress the vein. Alternatively, the valve member 106 may include an electromagnet (or multiple electromagnets) configured to compress the vein on its own (e.g., without relying on another magnetic structure, etc.). In another example, the valve member 106 may include two or more electromagnets configured to compress the vein, either in conjunction with one or more other magnetic structures or without. In general, the valve member 106 may include any suitable structure (or structures) configured to close or otherwise occlude the lumen of the vein, for example, by way of magnetic action on or through the structure(s), magnetic attraction between the structure(s) and another structure (or structures), etc.

Additionally, in this embodiment, the valve member 106 is configured as a normally open valve member (i.e., a passive open valve member). For example, the valve member 106 may include a biasing element, such as, for example, a spring, etc., and/or may be constructed from a resiliently deformable material, etc. configured to hold the valve member 106 open when not activated. Consequently, in the open position, the vein is not restricted by the valve member 106, whereby blood is free to flow through the lumen of the vein. In response to determining blood flow away from the heart based on the sensed characteristics, the controller 104 is then configured to activate the valve member 106 (e.g., against the biasing element, against the resilient nature of the valve member 106, etc.), which is then configured to compress the vein thereby occluding blood flow through the lumen. In response to a flow characteristic (e.g., favoring blood flow towards the heart, etc.), a defined time period, etc., the controller 104 is configured to deactivate (e.g., not activate or deactivate based on another signal, etc.) the valve member 106, whereby the valve member 106 is configured to return to its normally open position and permit blood flow in the vein.

Figure 2:
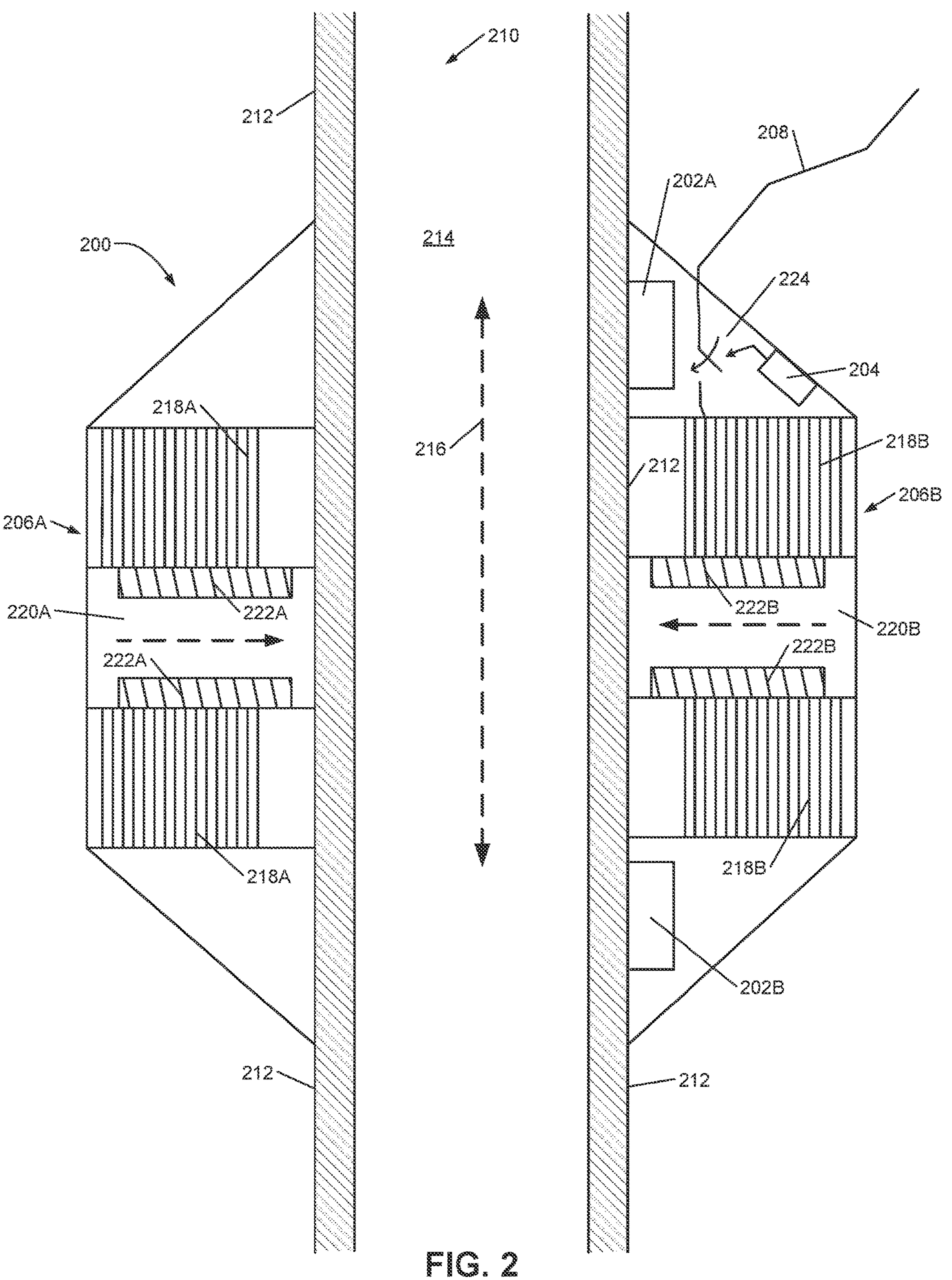
FIG. 2 is another example valve apparatus of the present disclosure, where the valve apparatus includes valve members for controlling blood flow in a vein of an individual.
Figure 3:
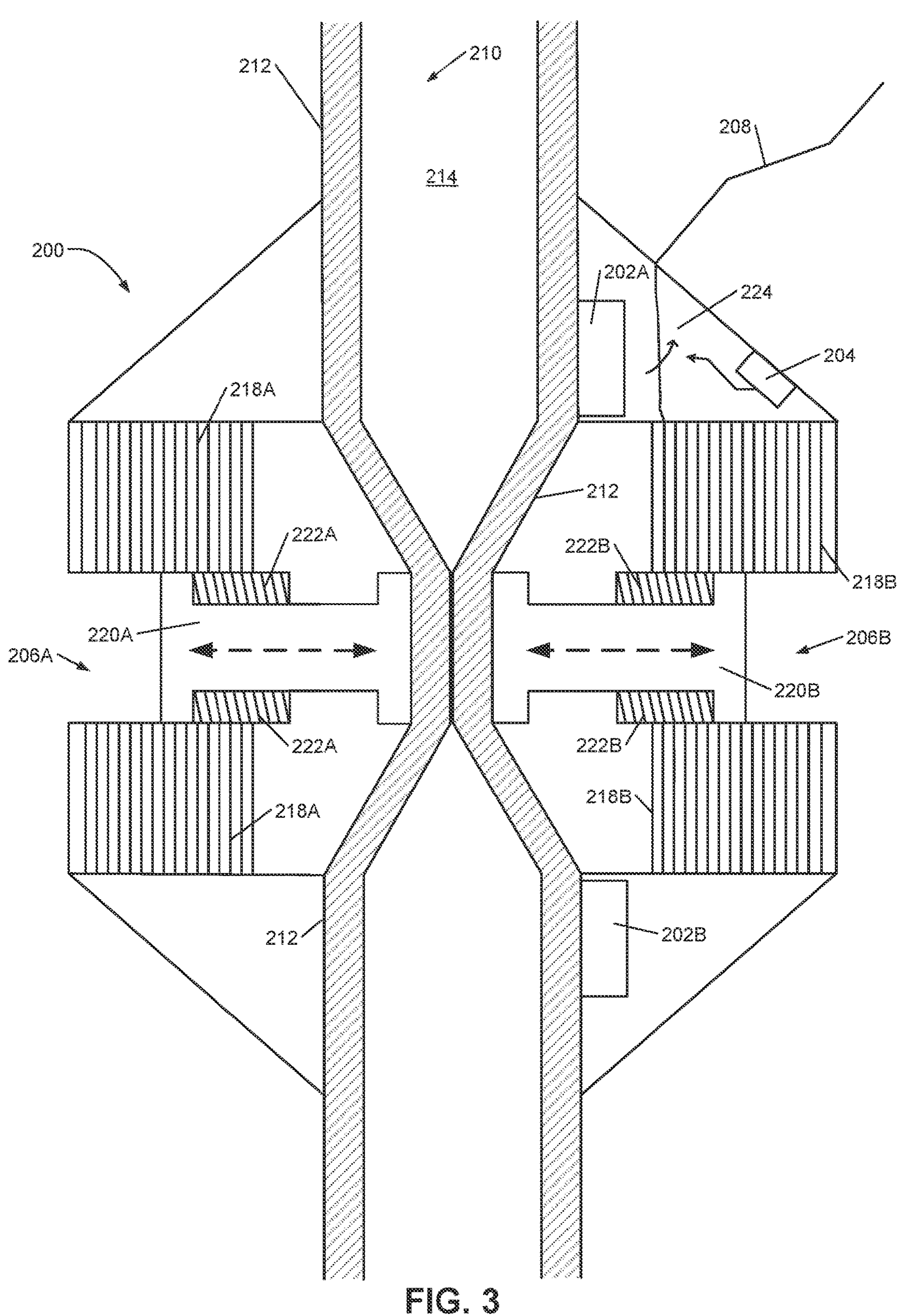
FIG. 3 is the example valve apparatus of FIG. 2 with the valve members in activated states for occluding blood flow in the vein.

FIGS. 2 and 3 illustrate an example valve apparatus 200 in which one or more aspects of the present disclosure may be implemented. The valve apparatus 200, as shown, is disposed about a vein 210 to affect blood flow (represented by arrow 216) in the vein 210. It should be understood that the vein 210 includes a wall 212, which, in turn, defines a lumen 214. In this example embodiment, the valve apparatus 200 generally includes two sensors 202A, 202B (e.g., pressure sensors, transducers of an ultrasonic flow meter, etc.), a controller 204 (e.g., a microcontroller, etc.) in communication with (e.g., via a wired connection, a wireless connection, etc.) the sensors 202A, 202B, two valve members shown as electromagnets 206A, 206B, and springs 222A, 222B adjacent to the electromagnets 206A, 206B.

In the example apparatus 200, the electromagnets 206A, 206B are positioned on opposing sides of the vein 210. Specifically, the electromagnets 206A, 206B are positioned along the exterior surface of the wall 212. Each electromagnet 206A, 206B includes a core 220A, 220B and a coil 218A, 218B wrapped about the core 220A, 220B.

The springs 222A, 222B are positioned adjacent to the cores 220A, 220B of the electromagnets 206A, 206B. In such an arrangement, the springs 222A, 222B are configured to bias the electromagnets 206A, 206B away from each other (and, for example, generally away from the wall 212 of the vein 210), and into normally open positions (e.g., as shown in FIG. 2). In some examples, the spring 222A and/or the spring 222B may be replaced with another suitable biasing element (or even omitted in other embodiments).

As shown in FIGS. 2 and 3, the sensors 202A, 202B are positioned on opposing sides of the electromagnet 206B. For example, the sensor 202A is positioned on a side of the electromagnet 206B proximal to a heart of the individual (e.g., a heart side of the valve apparatus 200, etc.), and the sensor 202B is positioned on a side of the electromagnet 206B distal to the heart (e.g., a limb side of the valve apparatus 200, etc.). With this arrangement, the sensors 202A, 202B may sense blood pressure levels on both sides of the electromagnet 206B, a flow rate of the blood flow, etc., and then provide signals (e.g., via a wired connection, wireless connection, etc.) to the controller 204 representing the sensed blood pressure levels, flow rate, etc. The controller 204 is configured to then determine the blood flow based on the sensed pressure levels flow rate, etc. from the two sensors 202A, 202B.

In the example of FIGS. 2 and 3, the sensors 202A, 202B, the controller 204, the electromagnets 206A, 206B, and the springs 222A, 222B are collectively positioned in one or more housings. For example, all of the components may be positioned in a single housing. Alternatively, the sensor 202A, the electromagnet 206A, and the spring 222A may be positioned in one housing, and the sensor 202B, the controller 204, the electromagnet 206B, and the spring 222B may be positioned in another housing. That said, other arrangements of the components relative to the vein 210 and/or other grouping of components in housings may be used within the scope of the present disclosure.

In the example apparatus 200, the sensors 202A, 202B, the controller 204, and the electromagnets 206A, 206B receive power from a power source via one or more wires. For clarity, FIGS. 2 and 3 show only one wire 208 extending to the electromagnet 206B via a switching device 224. Although not shown in FIGS. 2 and 3, it should be apparent that wires may also extend to the sensors 202A, 202B, the controller 204, and/or the electromagnet 206A. These wires may extend directly from the power source or from a power junction in the housing. Additionally, although not shown, the electromagnet 206A may receive power via the switching device 224 or another controllable switching device. In addition in this example embodiment, while also not shown, it should be apparent that wired connections may also extend, in this embodiment, between the controller 204 and the sensors 202A, 202B, and also between the controller 204 and the switching device 224 (or the electromagnets 206A, 206B). That said, it should again be appreciated that the components of the valve apparatus 200 may be powered otherwise in other embodiments, for example, wirelessly via indication, via self-contained power supplies incorporated into the individual components, etc. It should also be appreciated, again, that the controller 204, the sensors 202A, 202B, the switching device 224, and/or the electromagnets 206A, 206B may communicate with one another via one or more wireless connections in other embodiments (instead of or in addition to wired connections, etc.).

Figure 4:
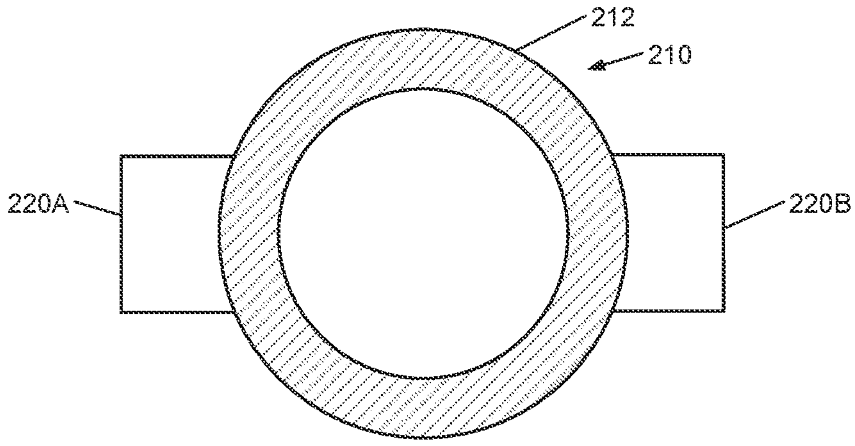
FIG. 4 illustrates the vein and the example valve members of the valve apparatus of FIG. 2, where the valve members are in deactivated states.

The controller 204 is configured to activate and/or deactivate (e.g., not activate, etc.) the electromagnets 206A, 206B. For example, the controller 204 may be configured to open the switching device 224 (as shown in FIG. 2). In such examples, the electromagnets 206A, 206B are de-energized, and in their normally open positions due to the springs 222A, 222B. During this time, the vein 210 may be generally open and have its typical shape such as a circular cross-sectional shape as shown in FIGS. 2 and 4.

Figure 5:
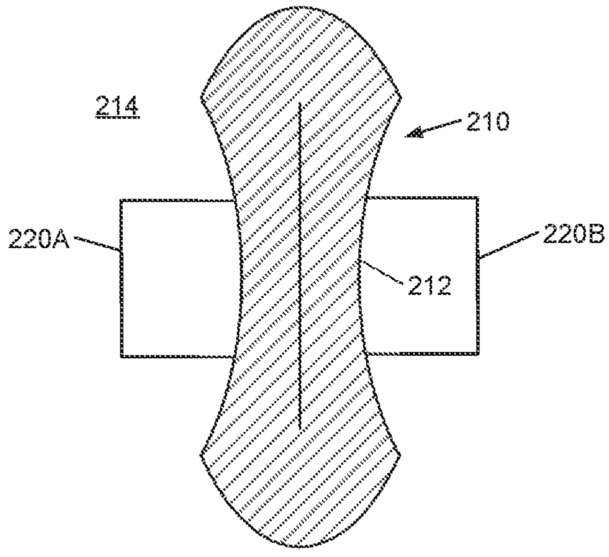
FIG. 5 illustrates the vein and the example valve members of the valve apparatus of FIG. 3, where the valve members are in activated states.

As shown in FIG. 3, in response to determining blood flow away from the heart, the controller 204 is configured to activate the electromagnets 206A, 206B to compress the vein 210 and occlude blood flow through the lumen 214. For example, the controller 204 may be configured to provide a control signal to close the switching device 224 (see FIG. 3) thereby allowing current to pass from the power source to the coils 218A, 218B. When the current is provided to the coils 218A, 218B, the cores 220A, 220B become magnetized. As a result, the cores 220A, 220B are configured (or otherwise caused) to move towards each other, as shown in FIG. 3. For example, when magnetized, the end of the core 220A adjacent to the vein 210 may be a north pole (or a south pole) of the electromagnet 206A, and the end of the core 220B adjacent to the vein 210 may be a south pole (or a north pole) of the electromagnet 206B (causing the cores 220A, 220B (e.g., the ends of the cores, etc.) to be attracted to each other and to move towards each other, etc.). As the cores 220A, 220B move towards each other, portions of the wall 212 of the vein 210 may be forced inward to deform the vein 210 and occlude blood flow through the lumen 214. During this time, the vein 210 may have an hourglass-like cross-sectional shape as shown in FIGS. 3 and 5, or another suitable cross-sectional shape, whereby the vein generally closes (or is substantially or at least partially restricted) with regard to flow of blood through the lumen 214.

If the controller 204 later determines blood through the vein 210 would flow towards the heart but for the compressed vein 210, based on the sensed blood pressure levels, flow rate, etc. (e.g., based on signals from the sensors 202A, 202B, etc.) and/or determines a defined period of time has elapsed, the controller 204 may deactivate (e.g., stop activating, etc.) the valve apparatus 200. In such examples, the controller 204 is configured to provide a control signal to open the switching device 224 (see FIG. 2) thereby interrupting current supplied to the coils 218A, 218B. Once the cores 220A, 220B are sufficiently demagnetized (due to the loss of current), the springs 222A, 222B force the cores 220A, 220B away from each other. As a result, the vein 210 may return to its typical shape (e.g., the circular cross-sectional shape of FIGS. 2 and 4).

In the valve apparatus 200, the ends of the cores 220A, 220B may include any desired shape configured to engage an outer portion of the vein. For instance, in some embodiments the ends of the cores 220A, 220B may include generally blunt, flat shapes configured to push on the outer portion of the vein. Alternatively, in some embodiments, the ends of the cores 220A, 220B may be rounded or arcuate to generally match or mirror a shape of the outer portion of the vein (e.g., to avoid potentially pinching the outer portion of the vein, etc.). What's more, in the valve apparatus 200, the ends of the cores 220A, 220B (as well as other components of the apparatus 200) may be constructed from suitable materials to inhibit corrosion, such as, for example, plastics, alloys, etc.

Figures 6, 7:
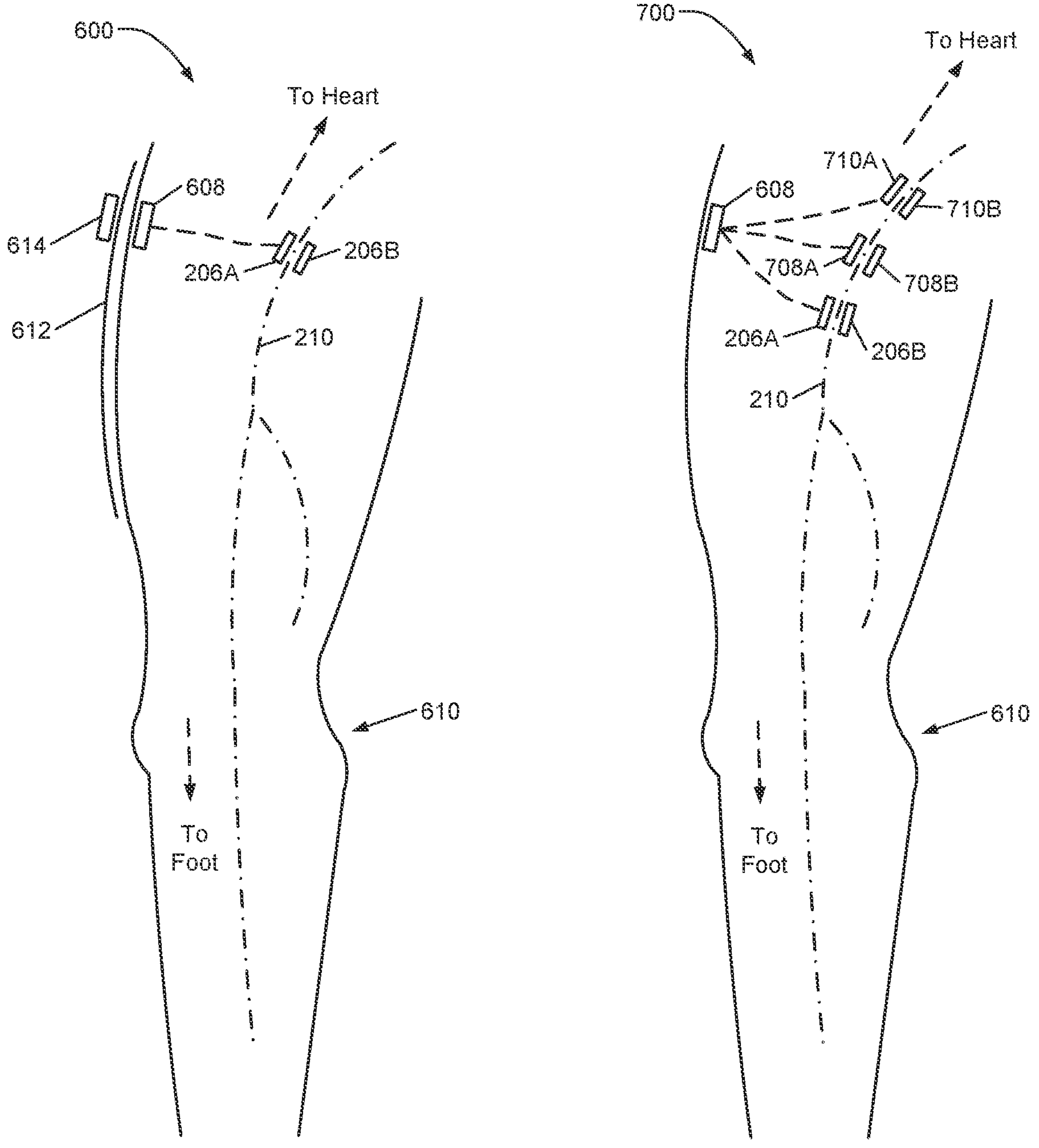
FIG. 6 is a diagram of an example valve apparatus including valve members positioned in a leg of an individual.
FIG. 7 is a diagram of an example valve apparatus including multiple sets of valve members positioned in a leg of an individual.

FIG. 6 illustrates another example valve apparatus 600 in which one or more aspects of the present disclosure may be implemented. The valve apparatus 600 includes the electromagnets 206A, 206B of FIG. 2, one or more sensors (not shown), a controller (not shown), and a battery 608 for powering the electromagnets 206A, 206B, the sensors and the controller. In the example of FIG. 6, the electromagnets 206A, 206B are positioned adjacent to the vein 210 (e.g., a femoral vein, etc.) in the upper thigh or groin area of a leg 610 of an individual, and the battery 608 is positioned in a subcutaneous tissue of the leg 610.

In the valve apparatus 600, the battery 608 may be charged as desired. For example, in FIG. 6, a power supply 614 is configured to charge (or recharge) the battery 608. For instance, the power supply 614 may be embedded within a garment 612 (a portion of which is shown in FIG. 6), attached to an inner surface of the garment 612, or attached to an outer surface of the garment 612. The garment 612 (a portion of which is shown in FIG. 6) may include a compression sock, compression shorts, or another suitable piece of clothing. When the garment 612 is worn by the individual, the power supply 614 is positioned adjacent to the skin of the individual and the battery 608, as shown in FIG. 6. If the power supply 614 is sufficiently close to the battery 608, the power supply 614 wirelessly charges (or recharges) the battery 608. In other examples, the battery 608 may include wires extending to (and/or through) an outer surface of the skin for connecting to the power supply.

FIG. 7 illustrates another example valve apparatus 700 in which one or more aspects of the present disclosure may be implemented. The valve apparatus 700 includes the electromagnets 206A, 206B of FIG. 2, additional sets of electromagnets 708A, 708B, 710A, 710B, and the battery 608 of FIG. 6 for powering the electromagnets 206A, 206B, 708A, 708B, 710A, 710B. In the example of FIG. 7, the electromagnets 206A, 206B, 708A, 708B, 710A, 710B are positioned adjacent to the vein 210 (e.g., a femoral vein, etc.) in the upper thigh or groin area of a leg 610 of an individual, and the battery 608 is positioned in a subcutaneous tissue of the leg 610. The battery 608 of FIG. 7 may be charged (or recharged) in a similar manner as described above relative to FIG. 6.

The electromagnets 708A, 708B, 710A, 710B may be similar to the electromagnets 206A, 206B. For example, the electromagnets 708A, 708B, 710A, 710B may be activated and/or deactivated to control the blood flow in the vein 210. In such examples, the valve apparatus 700 includes a controller (not shown) configured to provide signals to control the state of each of the electromagnets 206A, 206B, 708A, 708B, 710A, 710B. In other examples, the valve apparatus 700 may include multiple controllers in communication with each other. In such examples, one controller may be configured to control the state the electromagnets 206A, 206B, another controller may be configured to control the state the electromagnets 708A, 708B, and another controller may be configured to control the state the electromagnets 710A, 710B.

In the example of FIG. 7, the electromagnets 206A, 206B, 708A, 708B, 710A, 710B may be controlled (e.g., selectively activated, actuated, operated, etc.) to assist in pumping blood back to the heart. For example, the electromagnets may be controlled to sequentially activate such that they function as a peristaltic pump. For instance, the electromagnets 206A, 206B may be activated when blood flows away from the heart (as explained above). The electromagnets 708A, 708B and the electromagnets 710A, 710B may then also be activated for defined periods of time thereafter. In such examples, the defined periods of time are different to ensure the electromagnets 708A, 708B are activated before the electromagnets 710A, 710B. This sequential activation of the electromagnets 206A, 206B, 708A, 708B, 710A, 710B effectively alters the direction of blood flowing in the vein 210 and assists in pumping blood back to the heart.

As shown in FIG. 7, the valve apparatus 700 includes three sets of electromagnets 206A, 206B, 708A, 708B, 710A, 710B. In other examples, more or less electromagnets (and/or other suitable valve members) may be employed. For example, in some embodiments, the valve apparatus 700 may employ only two sets of electromagnets (or other valve members) about the vein 210 if their sequentially activation effectively pumps blood back to the heart. Alternatively, the valve apparatus 700 may employ four or more sets of electromagnets (or other valve members) about the vein 210 if desired.

Figure 8:
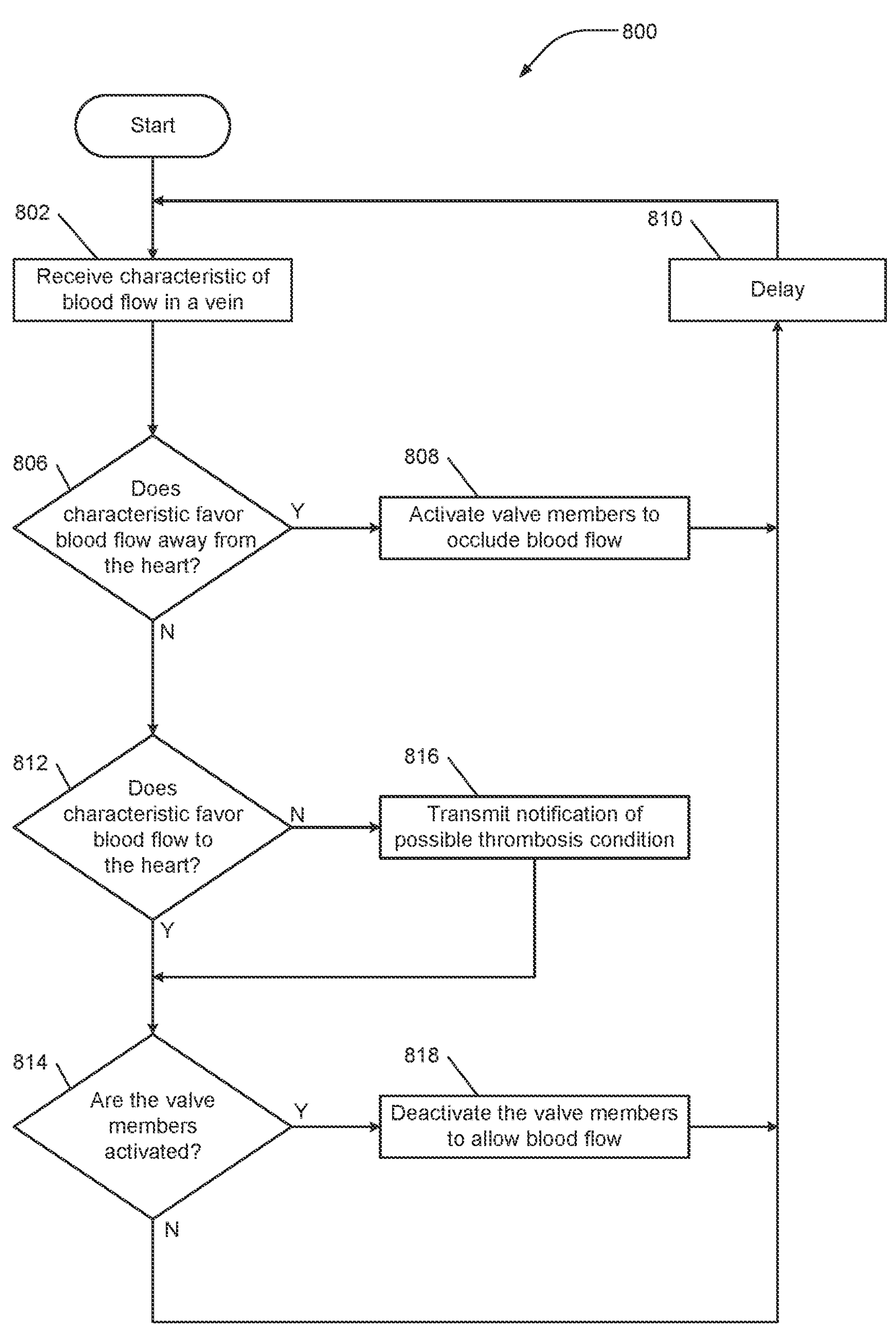
FIG. 8 is a flow diagram of an example method that may be implemented in connection with the example valve apparatus of FIG. 2.

FIG. 8 illustrates an example method 800 for use in controlling blood flow in a vein of an individual. The example method 800 is described with reference to the valve apparatus 200 of FIGS. 2 and 3. However, it should be understood that the method 800 is not limited to the valve apparatus 200, as the method 800, for example, may be implemented, at least in part, in another suitable valve apparatus, such as the valve apparatus 100 of FIG. 1, etc. Likewise, the valve apparatuses herein should not be understood to be limited to the example method 800.

In the example method 800, valve members (e.g., the electromagnets 206A, 206B, etc.) begin in their normally open position. The controller 204 receives one or more characteristics of blood flow in the vein 210, at 802, for example, from one or more sensors, and determines a direction of blood flow in the vein 210 based on the received characteristics. For example, the controller 204 may receive sensed pressure levels in the vein 210 on both sides of one of the valve members. The pressure levels may be sensed by the sensors 202A, 202B. The controller 204 may then compare the sensed pressure levels to determine the direction of blood flow. For instance, if the pressure level on the heart side of the valve member (e.g., the pressure sensed by the sensor 202A, etc.) is greater than the pressure level on the limb side of the valve member (e.g., the pressure sensed by the sensor 202B, etc.), then blood in the vein 210 is flowing away from the heart (e.g., retrograde flow, etc.). In other embodiments, the controller 204 may receive a sensed flow rate of the blood in the vein 210, and determine a direction of blood flow based on the flow rate.

At 806, the controller 204 determines whether the received characteristic(s) of blood in the vein 210 favor blood flow away from the heart. If yes, the controller 204 activates, at 808, the valve members to occlude blood flow and prevent reflux. For example, and as explained above, in the valve apparatus 200, the controller 204 may control a power source to supply current to the electromagnets 206A, 206B. As a result, the cores 220A, 220B become magnetized (and thereby attracted to each other) and move toward each other to occlude the vein 210. After an optional delay (e.g., a suitable defined period of time, etc.) in this example, at 810, the method 800 returns to 802 and the flow repeats as appropriate. Alternatively, the controller 204 may continue (e.g., continuously, etc.) to monitor blood flow in the vein, at 802, via the sensors, without waiting or delaying (whereby the method 800 generally returns to operation 802 without the delay).

If no, at 806, the controller 204 determines whether the received characteristic(s) of blood in the vein 210 favor flow towards the heart at 812. This determination may be made based on the received characteristics (e.g., pressure, flow, etc.) of the blood in the vein 210. For example, if the pressure level on the limb side of the valve member (e.g., the pressure sensed by the sensor 202B, etc.) is greater than the pressure level on the heart side of the valve member (e.g., the pressure sensed by the sensor 202A, etc.), then the controller 204 determines the blood in the vein 210 would flow towards the heart but for the compressed vein 210. As such, the received pressure levels favor flow towards the heart. For instance, a fixed volume venous compartment may be formed on the limb side of the valve member when the vein 210 is occluded. As blood crosses from arterial to venous circulation through a capillary bed, arterial blood is continuously moved to the fixed volume venous compartment causing the pressure on the limb side to increase. Additionally, a human leg includes a venous pumping mechanism known as a calf muscle pump. As the individual walks, calf muscles contract around veins embedded in the muscle tissue forcing blood towards the heart. When the vein 210 is occluded (e.g., due to the valve members, etc.), this physiologic mechanism of generating pressure may be enhanced as blood will be pumped into the fixed volume venous compartment.

If no, at 812, then blood may not be flowing through the valve members. This lack of blood flow may be due to a possible thrombosis (e.g., a clot, etc.) condition in the vein 210. In such scenarios, the controller 204 transmits, at 816, a notification (e.g., a signal, etc.) to a computing device indicating a possible thrombosis condition in the vein 210. As such, the individual, medical personnel, etc., may be alerted, and take appropriate action, if desired.

If yes, at 812, the controller 204 determines, at 814, whether the valve members are activated. If not, the method 800 proceeds to 810 (and to 802). If yes at 814, the controller 204 deactivates the valve members, at 818. For example, and as explained above, the controller 204 may control the power source to stop providing current to the electromagnets 206A, 206B. As a result, the cores 220A, 220B become demagnetized, and the springs 222A, 222B force the cores 220A, 220B to move away from each other. The method 800 then proceeds to 810 (and to 802).

Figure 9:
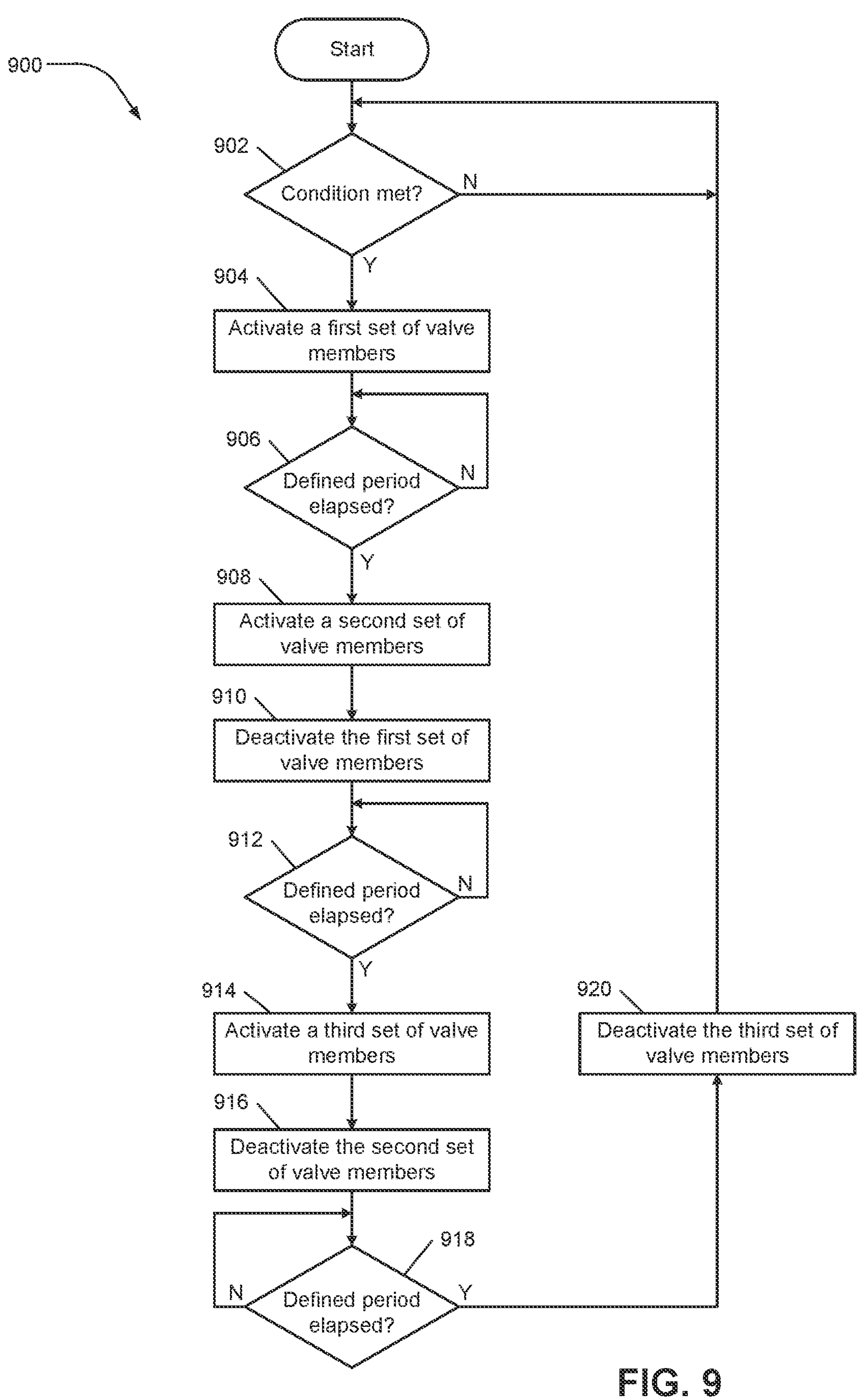
FIG. 9 is a flow diagram of an example method that may be implemented in connection with the example valve apparatuses of FIG. 7.

FIG. 9 illustrates another example method 900 for use in controlling blood flow in a vein of an individual and assisting in pumping blood back to the heart. The example method 900 is described with reference to the valve apparatus 700 including multiple sets of valve members. However, it should be understood that the method 900 is not limited to the valve apparatus 700, as the method 900, for example, may be implemented, at least in part, in another suitable valve apparatus, such as the valve apparatus 100 of FIG. 1. Likewise, the valve apparatuses herein should not be understood to be limited to the example method 900.

In the example method 900, the valve members begin in their normally open position. At 902, the controller determines if a condition has been met. For example, the controller may determine whether blood in the vein 210 is flowing away from the heart (e.g., retrograde flow, etc.) based on sensed pressure levels, a blood flow rate, etc. If no at 902, the method 900 returns to determining if a condition has been met. If yes at 902, the controller activates a first set of valve members (e.g., the electromagnets 206A, 206B of FIG. 7, etc.) furthest away from the heart at 904, as explained herein.

The controller then determines if a defined period of time has elapsed after activating the first set of valve members, at 906. If not, the method 900 returns to 906. If yes at 906, the controller activates a second set of valve members (e.g., the electromagnets 708A, 708B of FIG. 7), at 908. The second set of valve members are closer to the heart than the first set of valve members. After the second set of valve members are activated, the controller may deactivate (e.g., stop activating, etc.) the first set of valve members, at 910, as explained herein.

Next, the controller determines if another defined period of time has elapsed after activating the second set of valve members, at 912. If not, the method 900 returns to 912. If yes at 912, the controller activates a third set of valve members (e.g., the electromagnets 710A, 710B of FIG. 7, etc.), at 914. The third set of valve members are closer to the heart than the second set of valve members. After the third set of valve members are activated, the controller may deactivate the second set of valve members, at 916.

The controller then determines if another defined period of time has elapsed after activating the third set of valve members, at 918. If not, the method 900 returns to 918. If yes at 918, the controller may deactivate the third set of valve members at 920. The method 900, this example, then returns to 902. It should be appreciated that additional operations similar to above may be included in the method 900, in other embodiments, for additional valve members, etc.

As described above, the valve apparatuses of the present disclosure may include any suitable valve member(s) configured to close or otherwise occlude the lumen of a vein, for example, by way of magnetic action on or through the valve member(s), magnetic attraction between the multiple valve members, etc. In connection therewith, in some embodiments, a valve apparatus may include generally opposing valve members as described herein but where a central core portion of each of the valve members is configured to resiliently deform from a starting position toward the vein when magnetized (as opposed to the cores sliding relative to coils) and then to resiliently return to the starting position when demagnetized. In some embodiments, a valve apparatus may include a valve member extending generally around a vein (or that interacts with a sleeve extending generally around a vein) and configured, when magnetized, to constrict about the vein (or cause the sleeve to constrict about the vein) to thereby close or otherwise occlude a lumen of the vein. In some embodiments, a valve apparatus may include multiple valve members extending around a vein and configured, when magnetized, to move towards an opposing one of the valve members.

As used herein, a vein may include a native vein in a body and also may include a prosthetic conduit placed in the body that functions as a vein. As such, the valve members herein may be positioned along (e.g., positioned about, etc.) a native vein of an individual or a prosthetic conduit placed in the individual that functions as a vein. That said, in some embodiments, as described herein, the valve members are positioned along a native vein. This is because native veins are generally less thrombogenic, and therefore less susceptible to blood clots, than prosthetic conduits.

In view of the above, the valve apparatuses and methods herein provide for surgical options for treating conditions such as, for example, DVI, lymphedema, chronic wounds, etc., by placing one or more valve members outside of a lumen of a vein in an individual. For example, the valve members herein are surgically placed along exterior wall surfaces of the veins, and are not invasive into the lumens of the veins. Because the valve members are positioned outside the veins, and not within the lumens of the veins, individuals do not pose a risk of thrombosis and/or require anti-coagulation treatments due to the valves. Additionally, because the valve apparatuses are positioned outside the veins, components of the valve apparatuses do not directly contact blood in the lumens. As such, the components are resistant to bacterial seeding from remote sites (e.g., the lungs in the case of pneumonia, etc.). Further, the valve members do not cut, penetrate, puncture, or otherwise harm the vein when the valve members are activated. In fact, if any one of the valve members herein are placed along the femoral vein in the upper thigh or groin area (e.g., in the deep tissue) of an individual, the individual may not feel when the valve member is activated (e.g., when the vein is being compressed).

Additionally, the valve apparatuses herein may have a minimal footprint (e.g., about 1 cm×about 1 cm×about 2 cm footprint, etc.), and therefore may be amenable to implantation into the deep tissue of the individual. In some examples, the dimensions of the valve apparatuses may vary to accommodate differing patient anatomy and intended function. For example, dimensions may differ for patients with larger or smaller veins (whereby one or more dimensions of the apparatuses may be greater than or less than about 1 cm×about 1 cm×about 2 cm, etc.). Further, dimensions of the cores herein can be varied to change pumping capacity (e.g., cores with larger cross-sectional areas will generally displace more blood than cores with smaller cross-sectional areas, etc.).

Further, the valve apparatuses and methods herein may assist in occluding retrograde blood flow in a vein. As a result, swelling, chronic pain, and/or other undesirable experiences often felt by individuals afflicted with conditions, such as DVI, may be prevented. This prevention of retrograde blood flow may be accomplished by placing a single valve member and/or a single set of valve members along a single vein, or multiple sets of valve members along a single vein. Additionally, the single and/or multiple valve members of the assemblies herein may be configured to be controlled based on one or more sensed characteristics of the blood such as pressure, flow, etc. These characteristics may be used to ensure a minimal amount of force is applied to the vein as needed. For example, if the pressure within the vein is known, the controllers herein may be configured to dynamically control the valve member(s) to compress the vein wall with the least amount of force necessary to occlude flow. As such, the risk of developing stenosis due to trauma on the vein may be reduced.

In some embodiments, the valve apparatuses herein may assist in pumping blood back towards the heart when multiple sets of valve members are employed. In such examples, venous pressure may be lowered below normal physiologic pressure. Due to the decreasing venous pressure, an arterial-venous pressure gradient, and consequently a tissue perfusion pressure, may be increased. In some cases, decreased venous pressure promotes fluid shifts from an interstitial to a venous compartment thereby decreasing swelling in an individual experiencing lymphedema, and/or augments blood flow through a capillary bed thereby promoting wound healing in an individual.

The valve apparatuses herein may also be used for clearing debris in the vein to prevent possible clot conditions. For example, any one of the valve members and/or valve assemblies employed may be activated multiple times in a rapid fashion to clear thrombogenic debris (e.g., adherent platelets, microthrombi, etc.). In some examples, the multiple valve members may be repeatedly activated in a rapid alternating fashion to clear such debris.

Additionally, implantation of the valve apparatuses herein may require minimal technical expertise and limited invasive surgery. For example, because the valve apparatuses are extravascular devices, implantation of the apparatuses may require a routine procedure, not a vascular reconstruction. As such, most surgeons may possess the skills needed for implantation, not just vascular and endovascular surgeons. Further, due to the minimal footprint of the valve apparatuses and the avoidance of a vascular reconstruction, endoscopic implantation of the apparatuses may be employed. For example, similar to methods of endoscopic vein harvesting where endoscopes are used to free a vein of surrounding tissue prior to its removal, endoscopes can be used to prepare target veins for implantation and deliver of the valve apparatuses through small skin incisions.

Further, the valve apparatuses herein also allow for compatibility with current endovascular procedures, longevity, and ease of abandonment. For example, if a clot or stenosis at one of the valve apparatuses is discovered, it can be treated with a known endovascular procedure without compromising components of the valve apparatus. Additionally, the valve apparatuses may have more longevity than known surgical options due to, for example, the mechanical nature of the apparatuses. For example, known surgical options such as valvuloplasty are aimed at removing laxity in a vein wall or valve cusp. While this may have some effectiveness in preventing reflux, the treated veins and native valves are still subject to the same mechanisms that caused them to initially dilate and leak. When employing the valve apparatuses, recurrence of these conditions are less likely than with valvuloplasty because the valve apparatuses may be configured to completely occlude. Further, the valve apparatuses may be designed with mechanical failure points. For example, if one of the implemented valve apparatuses malfunctions, the valve apparatus may be designed to fail at a force/pressure above what is required for normal function but below what is technologically feasible with endovascular balloons. For instance, if the implemented valve apparatus causes thrombosis and/or stenosis, the apparatus may be decoupled from the vein without additional surgery. In such examples, a high pressure balloon may be used to fracture the apparatus at the manufactured failure points allowing the apparatus to fall away from the vein wall.

The valve apparatuses herein may also be at least partially resistance to user error. For example, and as explained herein, the valve members may be normally open. During this time, the valve members may consume little to no electrical power from a battery. As such, the battery may require less frequent charging. Therefore, employing normally open valve members may assist in reducing failures due to, for example, lack of compliance with charging requirements by the user.

It should be appreciated that the functions described herein, in some embodiments, may be described in computer executable instructions stored on a computer readable media, and executable by one or more processors. The computer readable media is a non-transitory computer readable storage medium. The computer readable media and one or more processors may be components of one of the controllers herein.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When a feature is referred to as being "on," "engaged to," "connected to," "coupled to," "associated with," "included with," or "in communication with" another feature, it may be directly on, engaged, connected, coupled, associated, included, or in communication to or with the other feature, or intervening features may be present. As used herein, the term "and/or" and the phrase "at least one of" includes any and all combinations of one or more of the associated listed items.

Although the terms first, second, third, etc. may be used herein to describe various features, these features should not be limited by these terms. These terms may be only used to distinguish one feature from another. Terms such as "first," "second," and other numerical terms when used herein do not imply a sequence or order unless clearly indicated by the context. Thus, a first feature discussed herein could be termed a second feature without departing from the teachings of the example embodiments.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

The foregoing description of example embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An apparatus for controlling blood flow in a vein of an individual, the vein including a wall defining a lumen through which blood flows, the apparatus comprising: at least one valve member configured to be positioned adjacent to an exterior surface of the vein of the individual and outside of the lumen of the vein, the at least one valve member configured to compress the vein when activated; at least one sensor configured to be positioned adjacent to the exterior surface of the vein, the sensor configured to sense one or more characteristics of blood flow through the lumen; and a controller coupled in communication with the at least one sensor and the at least one valve member, the controller configured to: receive, from the at least one sensor, a signal representing the one or more characteristics of blood flow; determine a direction of the blood flow based on the one or more characteristics; and in response to the determined direction of the blood flow being away from a heart of the individual, activate the at least one valve member to occlude the blood flow through the lumen away from the heart.

2. The apparatus of claim 1, wherein the controller is further configured to deactivate the at least one valve member in response to a subsequent determination that the one or more characteristics favor blood flow towards the heart.

3. The apparatus of claim 1, wherein the valve member includes a first side proximal to the heart and a second opposing side distal to the heart, wherein the at least one sensor includes a first sensor positionable adjacent to the first side of the valve member and a second sensor positionable adjacent to the second side of the valve member, and wherein the first sensor and the second sensor are configured to sense one or more characteristics of the direction of the blood flow through the lumen.

4. The apparatus of claim 1, further comprising at least one power source configured to provide power to the valve member, the at least one sensor, and the controller.

5. The apparatus of claim 4, wherein the at least one power source includes a battery configured to be positioned in a subcutaneous tissue of the individual.

6. The apparatus of claim 5, further comprising a garment including a power supply configured to wirelessly charge the battery.

7. The apparatus of claim 4, wherein the at least one valve member includes an electromagnet having a coil; and wherein the controller is configured, in order to actuate the at least one valve member, to control the at least one power source to provide current to the coil for activating the electromagnet to occlude the blood flow through the lumen away from the heart.

8. The apparatus of claim 4, wherein the at least one valve member includes a first electromagnet having a coil and a second electromagnet having a coil; and wherein the controller is configured, in order to actuate the at least one valve member, to control the at least one power source to provide current to the coil of the first electromagnet and the coil of the second electromagnet for activating the first electromagnet and the second electromagnet to occlude the blood flow through the lumen away from the heart.

9. The apparatus of claim 8, wherein the controller is configured, in order to deactivate the at least one valve member, to control the power source to stop providing current in response to the subsequent determination that the one or more characteristics favor blood flow towards the heart.

10. The apparatus of claim 1, further comprising one or more springs configured to be positioned adjacent to the at least one valve member, the one or more springs configured to bias the at least one valve member in a normally open position.

11. The apparatus of claim 1, wherein the at least one valve member is a first valve member, wherein the apparatus further comprises a second valve member configured to be positioned adjacent to the exterior surface of the vein, and between the first valve member and the heart, and wherein the controller is further configured, in response to the determined direction of the blood flow being away from a heart of the individual, to activate the second valve member a defined period of time after activating the first valve member to assist in pumping blood back to the heart.

12. A method for controlling blood flow in a vein of an individual with at least one valve member, the vein including a wall defining a lumen through which blood flows, the at least one valve member positioned adjacent to an exterior surface of the vein and outside of the lumen of the vein, the method comprising:

receiving, by a controller in communication with the at least one valve member, at least one signal from at least one sensor representing one or more characteristics of blood flow;

determining, by the controller, a direction of the blood flow based on the one or more characteristics; and in response to the determined direction of the blood flow being away from a heart of the individual, activating, by the controller, the at least one valve member to occlude the blood flow through the lumen away from the heart.

13. The method of claim 12, further comprising deactivating the valve member in response to a subsequent determination that the one or more characteristics favor blood flow towards the heart.

14. The method of claim 13, wherein the valve member includes a first side proximal to the heart and a second opposing side distal to the heart, and wherein receiving the at least one signal from the at least one sensor includes receiving a first signal, from a first sensor, representing a characteristic of the direction of the blood flow in the vein on the first side of the valve member and receiving a second signal, from a second sensor, representing a characteristic of the direction of the blood flow in the vein on the second side of the valve member.

15. The method of claim 14, wherein the at least one valve member includes a first electromagnet having a coil and a second electromagnet having a coil, and wherein activating the at least one valve member includes controlling a power source to provide current to the coil of the first electromagnet and the coil of the second electromagnet.

16. The method of claim 15, further comprising controlling the power source to stop providing current in response to the subsequent determination that a direction of the blood flow is towards the heart.

17. The method of method claim 12, wherein the at least one valve member is a first valve member, and wherein the method further comprises, in response to the determined direction of the blood flow being away from a heart of the individual, activating a second valve member a defined period of time after activating the first valve member to assist in pumping blood back to the heart.

* * * * *